United States Patent

Szantay et al.

[11] Patent Number: 4,464,535
[45] Date of Patent: Aug. 7, 1984

[54] PROCESS FOR THE PREPARATION OF EBURNAMONINE DERIVATIVES

[75] Inventors: Csaba Szantay; Lajos Szabo; György Kalaus; János Kreidl; György Visky; András Nemes; László Czibula; Mária Farkas nee Kirják, all of Budapest, Hungary

[73] Assignee: Richter Gedeon Vegyeszeti Gyar Rt., Budapest, Hungary

[21] Appl. No.: 438,288

[22] Filed: Nov. 1, 1982

[30] Foreign Application Priority Data

Mar. 11, 1981 [HU] Hungary .................. 3274/81

[51] Int. Cl.³ .................. C07D 461/00; C07D 455/00
[52] U.S. Cl. .................. 546/51; 546/70
[58] Field of Search .................. 546/51, 70

[56] References Cited

U.S. PATENT DOCUMENTS 3,770,724 11/1973 Warnant et al. .................. 546/51
4,146,643 3/1979 Pfäffli .................. 546/51 X
4,314,939 9/1982 Szantay et al. .................. 424/256 X
4,316,029 2/1982 Rossey .................. 546/51

Primary Examiner—Donald G. Daus
Assistant Examiner—Diana G. Rivers
Attorney, Agent, or Firm—Karl F. Ross; Herbert Dubno

[57] ABSTRACT

The invention relates to a new process for the preparation of eburnamonine derivatives of the general Formula I

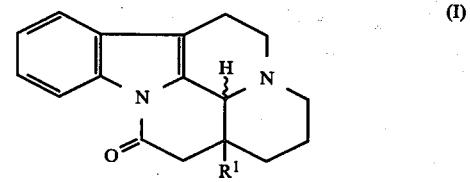

(wherein $R^1$ is an alkyl group having 1–6 carbon atoms) and optical and geometrical isomers thereof which comprises reacting a hydroxyimino-octahydro-indolo[2,3-a]quinolizine derivative of the general Formula II

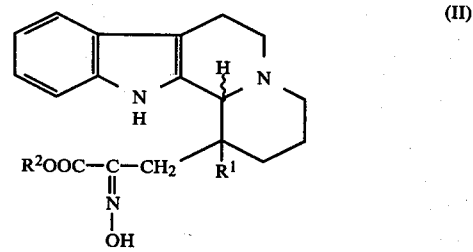

(wherein $R^1$ is as stated above and $R^2$ stands for an alkyl group having 1–6 carbon atoms being identical with or different from $R^1$, or a hydrogen atom) or an acid addition salt thereof in an organic protic solvent or solvent mixture with an inorganic base, optionally under the addition of water or an aqueous mineral acid, at a temperature between 60° C. and 200° C.

The compounds of the present invention are known drugs having blood pressure decreasing and cerebral vasodilatatory effect. The advantage of the process of the present invention is that it is readily feasible on industrial scale too, provides isomer-free pure products with high yield and requires the use of readily available simple starting materials.

4 Claims, No Drawings

PROCESS FOR THE PREPARATION OF EBURNAMONINE DERIVATIVES

The present invention relates to a new process for the preparation of eburnamonine derivatives of the Formula I

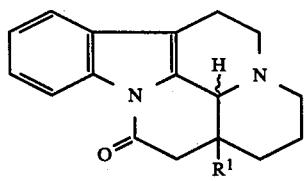

wherein $R^1$ is an alkyl group having 1-6 carbon atoms and optical and geometrical isomers thereof which comprises reacting a hydroxyimino-octahydroindolo[2,3-a]quinolizine derivative of the Formula II

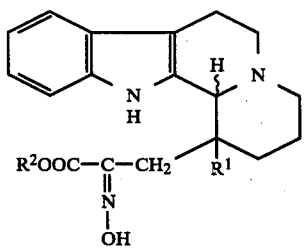

wherein $R^1$ is as stated above and $R^2$ stands for an alkyl group having 1-6 carbon atoms identical with or different from $R^1$, or a hydrogen atom, or an acid addition salt thereof in an organic protic solvent or solvent mixture with an inorganic base, optionally under the addition of water or an aqueous mineral acid, at a temperature between 60° C. and 200° C.

The process of the present invention can also be carried out by subjecting a hydroxyimino octahydroindolo[2,3-a]quinolizine derivative of the Formula II (wherein $R^1$ has the same meaning as stated above and $R^2$ stands for an alkyl group having 1-6 carbon atoms being identical with or different from $R^1$) or an acid addition salt thereof to basic hydrolysis at a temperature between 0° C. and 40° C., and reacting the hydroxyimino-octahydro-indolo[2,3-a]quinolizine derivative of the Formula II thus obtained (wherein $R^1$ is as stated above and $R^2$ stands for hydrogen) in an organic protic solvent or solvent mixture with an inorganic base, optionally under the addition of water or an aqueous mineral acid, at a temperature between 60° C. and 200° C.

The compounds of the Formula II, in which $R^1$ is as stated above and $R^2$ stands for hydrogen, and salts, optical and geometrical isomers thereof are biologically active new compounds. The scope of the present invention encompasses the said compounds and the process for their preparation as well.

In the above Formulae $R^1$ and $R^2$ may represent straight or branched chain alkyl groups having 1-6 carbon atoms (e.g. methyl, ethyl, n-propyl, isopropyl, sec. butyl, tert. butyl, n-pentyl, isopentyl, n-hexyl etc.).

Dextro-rotatory eburnamonine—being an alkaloid of the plant Hunteria eburnea—and laevo-rotatory eburnamonine and derivatives prepared therefrom (e.g. dextro-rotatory eburnamine; also called Linchanol) are pharmacologically valuable substances having significant blood pressure decreasing and cerebral vasodilatatory effect [Chimica Therapeutica 6, 221 (1971)]; Hungarian Pat. No. 157,687; [M. F. Bartlett and W. I. Taylor: J. Am. Chem. Soc. 82, 5941 (1960)]. According to recent pharmacological test results eburnamonine exhibits a more favorable effect on the oxygen supply of brain than vincamine [P. Lacroix, M. J. Quinicu, Ph. Linee, J. B. Le Poller: Arzn. Forsch. 29, (8), 1094 (1979)].

Several methods are known for the total syntheses of eburnamonines.

According to the article of M. F. Bartlett and W. I. Taylor [J. Am. Chem. Soc. 82, 5941 (1960)] racemic eburnamonine is synthesized in 8 steps by reacting triptamine with 2-hydroxy-3-ethyl-3'-($\beta$-carboxy-ethyl)furane-5-one—this compound can be prepared from p-ethylphenol by a complicated method—, reducing the compound thus obtained with lithium aluminum hydride and oxidizing the eburnamine thus formed with chromium trioxide to racemic eburnamonine.

According to the process of E. Wenkert and B. Wickberg [J. Am. Chem. Soc. 87, 1580 (1965)] 1-ethyl-1,2,3,4,6,7-hexahydro-indolo[2,3-a]quinolizinium perchlorate is subjected to an addition reaction with iodo acetic acid ester, the product thus obtained is reduced and the product formed is converted into racemic eburnamonine by alkaline treatment.

According to French patent application No. 71-00204 [J. Martel, G. Costerousse: C. A. 77, 152,432 v] racemic eburnamonine is prepared as follows: triptamine is reacted with ethyl bromo valerate, the product thus obtained is subjected to ring-closure by treatment with phosphorous oxychloride; the 1,2,3,4,6,7-hexahydro-12H-indolo[2,3-a]quinolizine is oxidized with dibenzoyl peroxide and thereafter treated with sodium hydride and triethyl phosphono acetate to give 1,2,3,4,6,7,12,12b-octahydro-indolo[2,3-a]quinolizidene-1-acetate, which is converted into eburnamonine with the aid of a Grignard reaction.

The common feature of the above three procedures is that they are suitable for the preparation of racemic eburnamonine only, there is no step in which resolution can be carried out and all the stereoisomers are constantly together. A further drawback of the Bartlett-Taylor and Wenkert-Wickberg methods resides in the fact that racemic eburnamonine is obtained in a complicated manner and stereoisomeric by-products are formed, which decrease the yield on the one hand and make the isolation and purification of the desired intermediates and end-products difficult on the other. For the above reasons the said processes are unsuitable for industrial scale production. An other disadvantage of the Martel-Costerousse process is that the multistep complicated synthesis comprises two steps which can be carried out on industrial scale production only with considerable difficulties—namely the treatment with sodium hydride and the Grignard reaction.

According to Trojanek et al. [Coll. Czech. Chem. Soc. 29, 433 (1964)] vincamine is first subjected to hydrolysis, and the vincamine acid thus obtained is oxidized into eburnamonine with chromium trioxide with a yield of 10.8%. In the same article the reductive splitting of vincamine with lithium aluminum hydride is also described; the yield of eburnamonine amounts to 10.2%. The greatest drawback of the above two methods resides in the very low yield.

According to Hungarian Patent specification No. 151,295 laevorotatory eburnamonine is prepared. The 14-carbomethoxy group of dextrorotatory vincamine is reacted with hydrazine, the hydrazone thus obtained is converted into the corresponding acide by treatment with nitrous acid and the acide thus formed is subjected to Curtius decomposition to yield eburnamonine. The disadvantage of the said process is that eburnamonine is obtained in many steps and the syntheses comprises the formation of an unstable acid azide, the latter step involving a high risk of explosion and requiring highly skilled labor.

According to Hungarian Pat. No. 166,475 optically active laevo- or dextrorotatory or racemic vincamine acid is oxidized with silver carbonate and/or manganese dioxide at elevated temperature into optically active laevo- or dextrorotatory or racemic eburnamonine respectively.

The common disadvantage of the above three methods is that all of them involve the preparation of a complicated pentacyclic compound possessing valuable therapeutical activity per se—namely the synthesis of vincamine—and the said compound is subsequently decomposed so that the number of the required chemical steps is very high.

According to Hungarian Pat. No. 166,766 from the cis-1-ethyl-1-(2'-hydroxy-2'-carboxy-ethyl)-1,2,3,4,6,7,12,12b-octahydro-indolo[2,3-a]quinolizine described in Hungarian Pat. No. 163.143 a mixture of eburnamine and eburnamonine, and from cis-1-ethyl-1-(2'-hydroxy-2'-alkoxycarbonyl-ethyl)-1,2,3,4,6,7,12,12b-octahydroindolo[2,3-a]quinolizine eburnamonine is prepared by oxidation. In the said oxidation reaction first the pentacyclic vincamine acid is formed, this compound is however not isolated but subjected to further oxidizing decomposition to yield eburnamonine. Oxidation is carried out at elevated temperature by using silver carbonate and/or manganese dioxide.

According to DOS No. 3,753,730 (BASF) eburnamonine is prepared from triptamine and formyl-ethyl-cyclopropane dicarboxylic acid diester by a complicated multistep synthesis. This process requires the use of quite specific reactants and is, hence, unsuitable for industrial scale manufacture.

In French patent application No. 77-22747 the preparation of laevorotatory eburnamonine is described. Dextrorotatory 14-oxo-15-hydroxyimino-3α,17α,-E-homoeburnane is first reacted with sodium hydroxide and ethoxy-ethanol at higher temperature, optionally under pressure, for a long reaction time and the desired product is prepared directly or after acidification. This process is accompanied by several drawbacks; the main disadvantage is the extremely long reaction time, moreover a complicated pentacyclic starting material must be previously synthesized and this is later decomposed.

The object of the present invention is to provide a process for the preparation of eburnamonine derivatives which can be carried out economically and simply on an industrial scale, which requires the use of starting materials available by simple and economical industrial scale methods and which gives rise to the selective formation of the desired stereoisomer or geometrical isomer respectively in pure form and with good yields.

It has been found that the starting materials of the Formula II excellently comply with the above requirements. According to Hungarian patent application Ser. No. 1753/81 (corresponding to U.S. application Ser. No. 387,676 filed June 11, 1982) the starting materials of the general Formula II can be prepared by a simple method with high yields directly in the form of the desired stereoisomer or geometrical isomer respectively.

The starting material of the formula (II) is prepared by treating a racemic or optically active compound of the formula (IV)

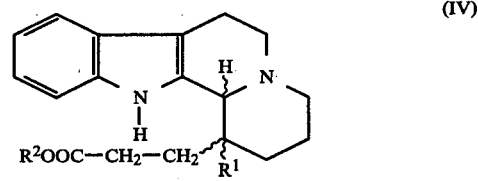

(IV)

with tert.-butyl nitrite in an aromatic hydrocarbon solvent and subsequently with an alkali metal tert. alcoholate. Optionally an alcohol of the formula $R^3$—OH where $R^3$ is $C_1$ to $C_6$ alkyl may be added to the reaction mixture.

The compound of the formula (IV) in racemic form is a compound wellknown in the art. The compound of the formula (IV) in racemic or optically active form is prepared by reducing an optically active or racemic compound of the formula (V)

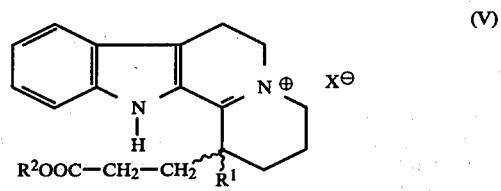

(V)

with an alkali metal hydride. The compound of the formula (IV) may also be prepared by catalytic hydrogenation of the compound of the formula (V). The compound of the formula (V) in racemic form is an old compound wellknown in the art. In the compound of the formula (V) $X^-$ stands for an acid residue or a $C_1$ to $C_6$ alcoholate.

Resolution of a racemic compound of the formula (IV) or formula (V) is carried out in any organic solvent or solvent mixture under inert reaction conditions. Suitable solvents include e.g. aliphatic or aromatic hydrocarbons optionally substituted by one or more halogens, such as dichloromethane, or alkanols having from 1 to 6 carbon atoms, such as methanol, ethanol, or mixtures thereof.

For catalytic hydrogenation of a compound of the formula (V), (Va) or (Vb)

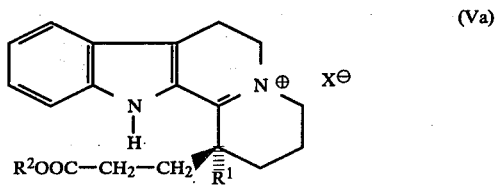

(Va)

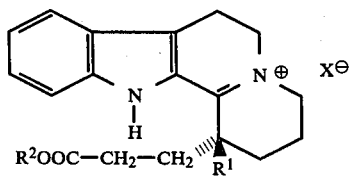
(Vb)

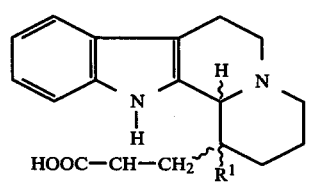
(III)

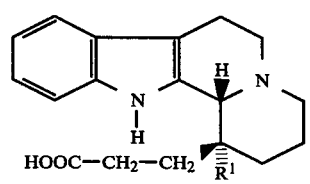
(IIIa)

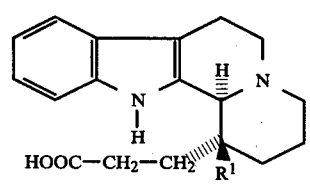
(IIIb)

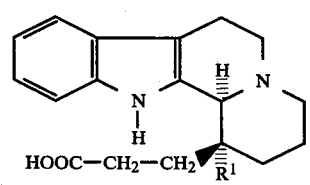
(IIIc)

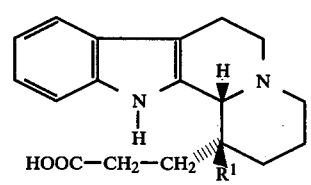
(IIId)

as a catalyst preferably palladium-on-charcoal is employed but the reaction may be successfully performed in the presence of any conventional hydrogenation metal catalyst, optionally precipitated on a carrier. Catalytic hydrogenation is carried out in the presence of an organic solvent or solvent mixture inert under the reaction conditions. Suitable solvents include aprotic dipolar solvents, such as dimethyl formamide, or protic solvents, such as alkanols having from 1 to 6 carbon atoms, such as methanol, ethanol, etc. or mixtures thereof.

The reduction of the compounds of the formula (V), (Va) and (Vb) is preferably carried out in the presence of sodium borohydride but for example lithium aluminum hydride may also be employed. The reduction is carried out in an alkanol having from 1 to 6 carbon atoms such as methanol, ethanol etc.

The alkaline hydrolysis of the compounds of the formulae (IV), (IVa), (IVb), (IVc) and (IVd)

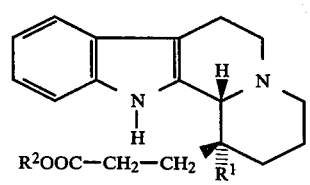
(IVa)

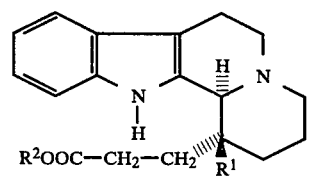
(IVb)

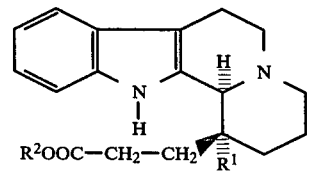
(IVc)

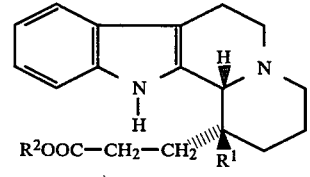
(IVd)

is performed in a mixture containing an inorganic base (e.g. alkali metal hydride, such as sodium hydride, an alkanol having 1 to 6 carbon atoms of water.

The acids of the formulae (III), (IIIa), (IIIb), (IIIc) and (IIId)

obtained by alkaline hydrolysis may be converted into a corresponding salt by a suitable base, or into other functional derivatives, e.g. acid halides, acid azides, etc.

When converting compounds of the formulae (IV), (IVa), (IVb), (IVc) and (IVd) into compounds of the formulae (II), (IIa), (IIb), (IIc) and (IId)

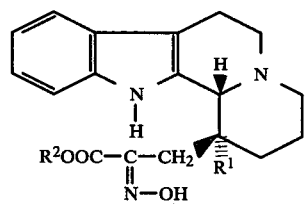
(IIa)

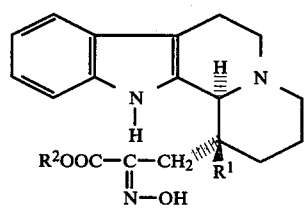
(IIb)

-continued

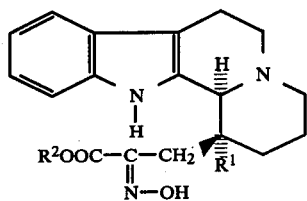

(IIc)

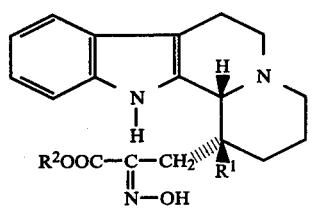

(IId)

respectively, as an aromatic hydrocarbon solvent for example benzene, toluene, xylene, etc. may be employed. Suitable alkali metal tertiary alcoholates include potassium or sodium alcoholates having 4 to 8 carbon atoms, e.g. potassium tert.-butylate, sodium tert.-butylate, potassium tert.-amylate, sodium tert.-amylate. Optionally an aprotic dipolar solvent, e.g. dimethyl formamide, dimethyl acetamide, etc. may also be added to the reaction mixture just as an alcohol of the formula $R^3$—OH.

According to the process of the present invention both racemic and optically active compounds of the Formula I can be prepared wherein the hydrogen atom in position 3 and the $R^1$ substituent in position 16 can be of $(\alpha,\alpha)$, $(\beta,\beta)$, $(\alpha,\beta)$ or $(\beta,\alpha)$ configuration. The stereoisomery or geometrical isomery and the optical activity of the compounds of the Formula I depend from and are identical with those of the starting materials of the Formula II. Thus if racemic compounds of the Formula II are used, racemic compounds of the Formula I are obtained. From optically active starting materials of the Formula II optically active compounds of the Formula I can be prepared. If in the starting material of the Formula II the hydrogen atom in position 3 and the $R^1$ substituent in position 16 are of $(\alpha,\alpha)$, $(\beta,\beta)$, $(\alpha,\beta)$ or $(\beta,\alpha)$ configuration respectively, the corresponding atoms and groups have the same configuration in the obtained end-products.

According to the process of the present invention as organic protic solvents, mono- or polyhydric alcohols, glycols or glycol ethers having high boiling point (e. g. ethylene glycol, diethylene glycol, diethylene glycol monoalkyl ethers) or mixtures thereof (e.g. a mixture of ethylene glycol and diethylene glycol) can be used. As inorganic base preferably alkali metal hydroxides (e.g. sodium hydroxide, potassium hydroxide etc.) can be used. As aqueous mineral acids the aqueous solutions of any suitable mineral acid (e.g. hydrochloric acid, sulfuric acid, phosphoric acid, etc.) can be used.

The reaction time depends on the temperature used and lies between 35 minutes and 3 hours.

As starting material both esters of the Formula II ($R^2$ is an alkyl group having 1-6 carbon atoms and $R^1$ has the same meaning as stated above) and the free acids of the Formula II ($R^1$ is as stated above and $R^2$ represents hydrogen) can be used. The acid addition salts of the compounds of the Formula II can serve as starting material as well. As acid addition salts such salts formed with any organic or inorganic acid can be employed (preferably the hydrochlorides).

According to an embodiment of the present invention esters of the Formula II are used as starting material which are first hydrolyzed in alkaline medium and the acids of the Formula II thus formed are subjected to the process of the present invention. Alkaline hydrolysis is carried out in an alkanol or glycol having 1-16 carbon atoms or water. As base inorganic bases, preferably an alkali metal hydroxide (e.g. sodium or potassium hydroxide) can be used. The acid of the Formula II (wherein $R^1$ is as stated above and $R^2$ stands for hydrogen) can be isolated, optionally after neutralization. The mixture can be made neutral by any organic or inorganic acid (e.g. citirc acid, acetic acid, etc.).

The advantages of the process of the present invention can be summarized as follows:
no difficultly and uncertainly available substances of vegetable origin are used, but the starting material can be easily and readily obtained by synthetic methods from easily available substances with high yields;
the starting material is available in the form of the desired stereoisomer or geometrical isomer suitable for further transformation;
the reaction conditions are more favorable and milder; namely shorter reaction time, lower temperature, atmospheric pressure, reaction steps comprising simple operations;
the process is readily feasible on industrial scale, economical and provides high yields;
the desired products are obtained in pure form, free from isomers.

It is highly advantageous that the starting materials can be prepared in pure state in the form of the corresponding stereoisomer or geometrical isomer, respectively. This ensures the purity of the end product and the absence of the isomers. A further advantage resides in the fact that it is not necessary to prepare a starting material more complicated than the desired end-product and possessing valuable therapeutical properties per se by circumstantial synthetic methods just to be subsequently decomposed into the desired compound. The starting materials used in the process of the present invention have a more simple structure than the desired end-products.

The racemic compounds prepared according to the process of the present invention can be separated into the optically active antipodes by resolution methods known per se, e.g. by forming diastereoisomeric salts, e.g. with D-tartaric acid. D-dibenzoyl tartaric acid, D-camphere-sulfonic acid, D-di-p-toluene tartaric acid.

Further details of the process claimed are to found in the following Examples without limiting the scope of the invention to the said Examples.

EXAMPLE 1

Racemic cis-eburnamonine

A mixture of 18.47 g. (0.05 mole) of (+)-cis-1-ethyl-(2'-methoxycarbonyl-2'-hydroxyimino-ethyl)-1,2,3,4,6,7,12,12b-octahydro-indolo[2,3-a]quinolizine, 100 ml. of ethylene glycol, 5.0 ml. of water and 6 g. (0.15 mole) of solid sodium hydroxide is stirred at 155°-160° C. for 3 hours. To the reaction mixture 200 ml. of water are added at 40° C. and the precipitated crude title compound is filtered off at 10° C. The crude product thus obtained (14 g) is dissolved in 50 ml. of dichloro-methane, the solution is treated with activated charcoal, filtered and the filtrate is evaporated at atmospheric pressure. To the residue 40 ml. of methanol are added, the mixture is filtered at 0° C. and the product is washed on the filter in portions with a total amount of 10 ml. of cold methanol. Thus 13.2 g. of the named compound are obtained. Yield 90%. Mp.: 199°-200° C.

EXAMPLE 2

Racemic cis-eburnamonine 21 g. (0.05 mole) of (+)-cis-1-ethyl-(2'-ethoxycarbonyl-2'-hydroxyimino-ethyl)-1,2,3,4,6,7,12,12b-octahydro-indolo[2,3-a]quinolizine-hydrochloride are dissolved in a mixture of 100 ml. of ethylene glycol, 5.0 ml. of water and 8 g. (0.2 mole) of solid sodium hydroxide and the process is carried out as described in Example 1. Thus 13.25 g of the named compound are obtained. Yield 90.2%, mp.: 199°-200° C.

EXAMPLE 3

(+)-cis-eburnamonine

A mixture of 20.3 g. of (0.05 mole) of (+)-1β-ethyl-1α-(2'-methoxycarbonyl-2'-hydroxyimino-ethyl)-1,2,3,4,6,7,12,12b-octahydro-indolo[2,3-a]quinolizine-hydrochloride, 100 ml. of diethylene glycol, 5.0 ml. of water and 8 g. (0.2 mole) of sodium hydroxide is reacted and worked up as described in Example 1. Thus 13 g. of the named compound are obtained. Yield 88.5%, mp.: 175° C., $[\alpha]_D^{20} = +94°$ (c=1, chloroform).

EXAMPLE 4

(−)-cis-eburnamonine

A mixture of 19.2 g. (0.05 mole) of (−)-1α-ethyl-1β-(2'-ethoxycarbonyl-2'-hydroxyimino-ethyl)-1,2,3,4,6,7,12,12bα-octahydro-indolo[2,3-a]quinolizine, 100 ml. of ethylene glycol, 5.0 ml. of water and 8.1 g. (0.15 mole) of solid potassium hydroxide is reacted and worked up as described in Example 1. Thus 13.0 g. of the named compound are obtained. Yield: 90%. Mp.: 174°-175° C.

$[\alpha]_D^{20} = -93°$ (c=1, chloroform).

EXAMPLE 5

Racemic trans-eburnamonine 21 g. (0.05 mole) of (+)-trans-1-ethyl-1-(2'-ethoxycarbonyl-2'-hydroxyimino-ethyl)-1,2,3,4,6,7,12,12b-octahydro-indolo[2,3-a]quinolizine-hydrochloride are dissolved in a mixture of 100 ml. of ethylene glycol, 5.0 ml. of water and 8.0 g. (0.2 mole) of solid sodium hydroxide and the reaction is carried out in an analogous manner to Example 1. Thus 12.48 g. of the named compound are obtained. Yield: 85%. Mp.: 135°-135.5° C.

EXAMPLE 6

(+)-trans-eburnamonine

A mixture of 18.4 g. (0.05 mole) of (+)-1α-ethyl-1β-(2'-methoxycarbonyl-2'-hydroxyimino-ethyl)-1,2,3,4,6,7,12,12bβ-octahydro-indolo[2,3-a]quinolizine, 100 ml. of diethylene glycol monomethylether, 5 ml. of water and 6.0 g. (0.15 mole) of solid sodium hydroxide is reacted and worked up as described in Example 1. Thus 12.35 g. of the named compound are obtained. Yield: 84%. Mp.: 145°-146° C.

$[\alpha]_D^{20} = +167.4°$ (c=1, chloroform).

EXAMPLE 7

(−)-trans-eburnamonine

A mixture of 20.3 g. (0.05 mole) of (−)-1β-ethyl-1α-(2'-methoxycarbonyl-2'-hydroxyimino-ethyl)-1,2,3,4,6,7,12,12bα-octahydro-indolo[2,3-a]quinolizine-hydrochloride, 100 ml. of ethylene glycol, 5.0 ml. of water and 6.0 g. (0.2 mole) of solid sodium hydroxide is reacted and worked up as described in Example 1. Thus 12.7 g. of the named compound are obtained, yield 86.5%. Mp: 145°-146° C.

$[\alpha]_D^{20} = -168.1°$ (c=1, chloroform).

EXAMPLE 8

Racemic cis-eburnamonine

A mixture of 3.69 g. (0.01 mole) of (+)-1-ethyl-1-(2'-methoxycarbonyl-2'-hydroxyimino-ethyl)-1,2,3,4,6,7,12,12b-octahydro-indolo[2,3-a]quinolizine, 10 ml. of ethylene glycol and 0.8 g. (0.02 mole) of solid sodium hydroxide is stirred at 135° C. for 30 minutes, whereupon to the mixture 15.0 ml. of water are added and the pH is adjusted to the value of about 1-1.5 by adding about 3.2 ml. of a concentrated aqueous hydrochloric acid solution. The solution is stirred at 60° C. for 30 minutes, whereupon 10 ml. of dichloromethane and 50 ml. of water are added. The mixture is made alkaline to pH 9 by the addition of 1.7 ml. of a concentrated aqueous ammonium hydroxide solution under stirring. The layers are separated, the aqueous phase is extracted twice with 10 ml. of dichloromethane each. The united organic layers are dried over solid anhydrous sodium sulfate, filtered and the solvent is removed from the filtrate by atmospheric distillation. To the residue 5.5 ml. of methanol are added. After cooling the precipitated crystals are filtered off, washed twice with 1.5 ml. of cold methanol each and dried. Thus 2.72 g. of the named compound are obtained. Yield: 92%; mp.: 199°-200° C.

$[\alpha]_D^{20} = +0°$ (c=1, chloroform)

EXAMPLE 9

Racemic cis-eburnamonine

One proceeds as described in Example 8 except that 3.85 g. of (+)-1-ethyl-1-(2'-ethoxycarbonyl-2'-hydroxyimino-ethyl)-1,2,3,4,6,7,12,12b-octahydro-indolo[2,3-a]quinolizine are used as starting material. Thus 2.7 g. of the named compound are obtained, yield 91.8%. Mp.: 199°-200° C.

$[\alpha]_D^{20} = \pm 0°$ (c=1, chloroform).

EXAMPLE 10

Racemic cis-eburnamonine

One proceeds as described in Example 8 except that 4.07 g. of (+)-1-ethyl-1-(2'-methoxycarbonyl-2'-hydroxyimino-ethyl)-1,2,3,4,6,7,12,12b-octahydro-indolo[2,3-a]quinolizine-hydrochloride is used as starting material and the 0.8 g. of solid sodium hydroxide is replaced by 1.2 g. (0.03 mole) of solid sodium hydroxide. Thus 2.71 g. of the named compound are obtained. Yield: 91.9%, mp.: 198°-200° C.

$[\alpha]_D^{20} = \pm 0°$ (c=1, chloroform).

EXAMPLE 11

(−)-cis-eburnamonine

A mixture of 3.69 g. (0.01 mole) of (−)-1-α-ethyl-1β-(2'-methoxycarbonyl-2'-hydroxyimino-ethyl)-

1,2,3,4,6,7,12,12bα-octahydro-indolo[2,3-a]quinolizine, 10 ml. of ethylene glycol and 0.8 g. (0.02 mole) of solid sodium hydroxide is stirred at 160° C. for 5 minutes, whereupon 15.0 ml. of water are added and the pH is adjusted to the value of 1–1.5 by adding 3.2 ml. of a concentrated hydrochloride acid. The solution is stirred at 60° C. for 30 minutes, whereupon 10 ml. of dichloromethane and 50 ml. of water are added. The mixture is made alkaline (pH=9) by the addition of 1.7 ml. of a concentrated ammonium hydroxide solution under stirring. The layers are separated and the aqueous phase is extracted twice with 10 ml. of dichloro-methane each. The combined organic phases are dried over solid anhydrous sodium sulfate, filtered, the solvent is distilled off from the filtrate and to the residue 5.5 ml. of methanol are added. The solution is cooled to a temperature below 10° C., the precipitated product is filtered off, washed twice with 1.5 ml. of methanol and dried. Thus 2.72 g. of the named compound are obtained. Yield 92%, mp.: 174°–175° C.

$[\alpha]_D^{20} = -93.1°$ (c=1, chloroform).

EXAMPLE 12

(+)-cis-eburnamonine

One proceeds according to Example 11 except that 3.69 g. of (+)-1β-ethyl-1α-(2'-methoxycarbonyl-2'-hydroxyimino-ethyl)-1,2,3,4,6,7,12,12bβ-octahydroindolo[2,3-a]quinolizine are used as starting material. Thus 2.72 g. of the named compound are obtained, yield: 92%. Mp.: 175° C.:

$[\alpha]_D^{20} = 94°$ (c=1, chloroform).

EXAMPLE 13

Racemic 1-ethyl-1-(2'-hydroxycarbonyl-2'-hydroxyimino-ethyl)-1,2,3,4,6,7,12,12b-octahydroindolo[2,3-a]quinolizine A mixture of 9.25 g. (0.025 mole) of (+)-ethyl-1-(2'-methoxycarbonyl-2'-hydroxyimino-ethyl)-1,2,3,4,6,7,12,12b-octahydro-indolo[2,3-a]quinolizine, 8.0 g (0.2 mole) of solid sodium hydroxide, 100 ml. of ethanol and 5.0 ml. of water is acidified to a pH value of 6.3 by the addition of a solution of 16 g. of citric acid in 150 ml. of water. The solution is extracted six times with 50 ml. of dichloromethane each. The united organic phases are extracted with a saturated sodium chloride solution, the layers are separated, the organic phase is dried over anhydrous sodium sulfate, filtered and the filtrate is evaporated. To the residue 50 ml. of ether are added, the mixture is heated to boiling, then cooled, the precipitated product is filtered and dried. Thus 7.2 g. of the named compound are obtained, yield 81%. Mp.: 124° C. (decomposition).

IR(KBr): ν=3400 (NH, OH); 1635 (COOH) cm$^{-1}$.
NMR (DMSO-d$_6$): δ=9.9 s (COOH); 3.5 s (CH in position 3); 1 s (CH$_3$); 6.95–7.35 m, 4 (aromatic H).

EXAMPLE 14

Racemic cis-eburnamonine

A mixture of 3.55 g. (0.01 mole) of (+)-1-ethyl-1-(2'-hydroxycarbonyl-2'-hydroxyimino-ethyl)-1,2,3,4,6,7,12,12b-octahydro-indolo[2,3-a]quinolizine, 15 ml. of ethylene glycol and 1.2 g. (0.03 mole) of solid sodium chloride is stirred at 135° C. for 30 minutes whereupon 20 ml. of water are added, the pH is adjusted to a value of 1–1.5 by adding about 3.5 ml. of concentrated hydrochloric acid, whereupon it is made alkaline (pH 9) by the addition of a concentrated aqueous ammonium hydroxide solution. The mixture is extracted three times with 25 ml. of dichloromethane each. The united dichloro-methane phases are dried over solid anhydrous sodium sulfate, filtered, from the filtrate the solvent is removed by atmospheric distillation and to the residue 5 ml. of methanol are added. The mixture is cooled and the precipitated product is filtered off, washed with some methanol and dried. Thus 2.65 g. of the named compound are obtained. Yield 90%. Mp.: 198°–200° C.

$[\alpha]_D^{20} = \pm 0°$ (c=1, chloroform).

The following examples are directed to the preparation of starting materials.

PREPARATION EXAMPLE 1

Resolution of 1-(methoxycarbonylethyl)-1-ethyl-1,2,3,4,6,7-hexahydro-12H-indolo[2,3-a]quinolizinium methanolate (hereinafter acrolamin methanolate) by dibenzoyl-l-tartaric acid.

100.0 g (0.2699 moles) of acrolamin methanolate are dissolved in 200.0 ml of dichloromethane at room temperature, whereupon a solution of 100.0 g of dibenzoyl-l-tartaric acid monohydrate (0.2673 moles) in 400.0 ml of dichloromethane is added under stirring. The mixture is stirred at room temperature for one hour, whereupon the precipitated substance is filtered off, washed with dichloromethane and dried. 91.84 g (0.1322 moles) of 1-(methoxycarbonyl-ethyl(-α-ethyl-1,2,3,4,6,7-hexahydro-12H-indolo-(2,3-a)tartarate are obtained.

Yield: 98.0% (calculated for the α-ethyl form).
$[\alpha]_D^{20} = -68.6°$ (c=1, in DMF)
Base content: 48.49% (theoretical: 48.73%)
Melting point: 139.5° to 140° C.

From the compound obtained the corresponding base is set free, whereafter the salt of the methanolate and perchlorate is also prepared.

1-(methoxycarbonylethyl)-α-ethyl-1,2,3,4,6,7-hexahydro-12H-indolo(2,3-a)quinolizinium methanolate: melting point:
151° to 152° C.
$[\alpha]_D^{20} = -27.6°$ (c=1, DMF)
1-(methoxycarbonylethyl)-α-ethyl-1,2,3,4,6,7-hexahydro-12H-indolo(2,3-a)quinolizinium
HClO$_4$: melting point: 178° to 180° C.
$[\alpha]_D^{20} = -23.5°$ (c=1, DMF)

From the mother liquor of the resolution the corresponding salts of the β-ethyl antipode may be prepared, after setting free the base.

PREPARATION EXAMPLE 2

The resolution of 1-(methoxycarbonylethyl)-1-ethyl-1,2,3,4,6,7-hexahydro-12H-indolo(2,3-a)quinolizinium methanolate by dibenzoyl-l-tartaric acid.

100.0 g (0.2699 moles) of acrolamin-methanolate are dissolved in 200.0 ml of dichloromethane at room temperature, whereupon a solution of 100.0 g (0.2673 moles) of dibenzoyl-d-tartaric acid in 400.0 ml of dichloromethane is added. After stirring at room temperature for one hour the reaction mixture is filtered, washed with dichloromethane and dried.

91.7 g (0.1320 moles) of 1-(methoxycarbonylethyl)-β-ethyl-1,2,3,4,6,7-hexahydro-12H-indolo(2,3-a)quinolizinium dibenzoyl tartarate are obtained.

Yield: 97.8% (calculated for the β-ethyl form).
$[\alpha]_D^{20} = +68.8°$ (c=1, DMF)
Base content: 48.5% (theoretical: 48.73%)
Melting point: 139° to 140° C.

From the crude compound obtained the corresponding methanolate and perchlorate salts can be prepared, afteer setting free the corresponding base.

1-(methoxycarbonylethyl)-β-ethyl-1,2,3,4,6,7-hexahydro-12H-indolo(2,3-a)quinolizinium methanolate: melting point: 150° to 152° C.

$[\alpha]_D^{20} = +27.8°$ (c=DMF)

1-(methoxycarbonylethyl)-β-ethyl-1,2,3,4,6,7-hexahydro-12H-indolo(2,3-a)quinolizinium perchlorate: melting point: 178.5° to 180° C.

$[\alpha]_D^{20} = +24°$ (c=1 DMF)

From the mother liquor of the resolution the corresponding salts of the α-ethyl antipode can also be prepared, after setting free the base.

PREPARATION EXAMPLE 3

(−)-1β-(methoxycarbonylethyl)-1α-ethyl-1,2,3,4,6,7,12,12bα-octahydro-indolo[2,3-a]quinolizine 34.7 g (0.05 moles) of (−)-1β-methoxycarbonylethyl)-1α-ethyl-1,2,3,4,6,7-hexahydro-12H-indolo(2,3-a)quinolizine-5-ium (−)dibenzoyltartarate in 70 ml of dimethyl formamide, in the presence of 0.25 g of a 10% palladium-on-charcoal catalyst are hydrogenated for 2.5 hours, at 40° C., under atmospheric pressure. The catalyst is filtered off and is then washed with altogether 10 ml of dimethyl formamide in two portions. To the filtrate 200 ml of a 5% aqueous methanol solution is poured under vigorous stirring. The (−)-dibenzoyl tartarate of the title compound is precipitated. The product is washed with altogether 10 ml of cold methyl alcohol in two portions and dried.

Yield: 26 g (75%)

Melting point: 150° to 152° C.

$[\alpha]_D^{20} = -120.1°$ (c=2 DMF)

PREPARATION EXAMPLE 4

(+)-1α-(methoxycarbonylethyl)-1β-ethyl-1,2,3,4,6,7,12,12β-octahydro-indolo(2,3-a)quinolizine.

Following the procedure described in Example 3 but starting from 34.7 g (0.05 moles) of (+)-1α-(methoxycarbonyl-ethyl)-1β-1,2,3,4,6,7-hexahydro-12H-indolo(2,3-a)quinolizine-5-ium (+)-dibenzoyltartarate, the title compound is obtained, weighing 25.5 g (73.5%).

Melting point: 150° to 151° C.

$[\alpha]_D^{20} = +119.8°$ (c=2 DMF)

PREPARATION EXAMPLE 5

(+)-1β-(methoxycarbonylethyl)-1α-ethyl-1,2,3,4,6,7,12,12bβ-octahydro-indolo(2,3-a)quinolizine.

4.39 g (0.01 moles) of (−)-1β-(methoxycarbonylethyl)-1-α-ethyl-1,2,3,4,6,7-hexahydro-12H-indolo(2,3-a)quinolizine-5-ium perchlorate are suspended in 100 ml of methyl alcohol at 60° C., and at the same temperature 1.2 g of sodium borohydride are added in one hour, in more portions, whereupon the mixture is stirred for a further one hour. 70 ml of methyl alcohol are distilled off from the reaction mixture, the residue is stirred at 0° C., then washed by covering with cold methyl alcohol and washed to neutral with distilled water. 1.7 g (50%) of the title compound are obtained, melting at 108° to 109° C.

$[\alpha]_D^{20} = +69.7°$ (c=1, CHCl₃).

PREPARATION EXAMPLE 6

(−)-1α-(methoxycarbonylethyl)-1β-ethyl-1,2,3,4,6,7,12,12bα-octahydro-indolo(2,3-a)quinolizine.

Following the procedure described in Example 5 but starting from 4.39 g (0.01 moles) of (+)-1α-(2′-methoxycarbonylethyl)-1β-ethyl-1,2,3,4,6,7-hexahydro-12H-indolo(2,3-a)quinolizine-5-ium perchlorate, 1.73 g (51%) of the title compound are obtained, melting at 108° to 109° C.

$[\alpha]_D^{20} = -68.9°$ (c=1, CHCl₃).

PREPARATION EXAMPLE 7

Resolution of racemic trans 1-(methoxycarbonylethyl)-1-ethyl-1,2,3,4,6,7,12,12b-octahydro-indolo(2,3-a)quinolizine.

34 g (0.1 moles) of the title compound are suspended in 400 ml of methyl alcohol at 55° C. and a solution of 15 g (0.1 moles) of D-tartaric acid in 40 ml of methyl alcohol of 55° C. is added at the same temperature. The homogeneous solution is cooled to 15° C. The precipitated (+)-1β-(methoxycarbonylethyl)-1α-ethyl-1,2,3,4,6,7,12,12bβ-octahydro-indolo(2,3-a)quinolizine-5-ium D-tartarate is filtered and washed with altogether 50 ml of cold methanol in two portions. 24.1 g (98.3%) of the above compound are obtained, melting at 213° to 215° C.

$[\alpha]_D^{20} = +44.8°$ (c=1 DMF).

The corresponding base is set free as follows:

The product is dissolved in 200 ml of water, the pH is adjusted to 9 with aqueous ammonia and the mixture is extracted with altogether 120 ml of dichloromethane, in three portions. After drying the solution is evaporated and the obtained oily residue is boiled with 30 ml of methanol. 15.5 g (91.5%) of (+)-1β-(methoxycarbonylethyl)-1α-ethyl-1,2,3,4,6,7,12,12bβ-octahydro-indolo(2,3-a)quinolizine are obtained, melting at 108.5° to 109° C.

$[\alpha]_D^{20} = +70.1°$ (c=1, CHCl₃).

From the methanolic mother liquor of the resolution the other optically active isomer is isolated. It is evaporated to 100 ml, diluted with 200 ml of water and after adjusting the pH to 9 by aqueous ammonia, it is extracted with altogether 120 ml of dichloromethane in three portions. The mixture is dried, evaporated and the oily residue is boiled with 30 ml of methanol.

15.1 g (89%) of (−)-1α-(methoxycarbonylethyl)-1β-ethyl-1,2,3,4,6,7,12,12bα-octahydro-indolo(2,3-a)quinolizine are obtained, melting at 109° C.

$[\alpha]_D^{20} = -69.4°$ (c=1, CHCl₃).

PREPARATION EXAMPLE 8

(+)-1β(carboxyethyl)-1α-ethyl-1,2,3,4,6,7,12,12bβ-octahydro-indolo(2,3-a)quinolizine.

6.8 g (0.02 moles) of (+)-1β-(methoxycarbonylethyl)-1α-ethyl-1,2,3,4,6,7,12,12bβ-octahydro-indolo(2,3-a)quinolizine, 80 mo of methanol, 4 ml of water and 2 g of sodium hydroxide are refluxed for one hour, whereupon 50 ml of the mixture are distilled off under reduced pressure, 80 ml of water are added and the pH is adjusted to 6.5 with a 1M aqueous citric acid solution, at 60° C. The title compound is filtered off at 20° C. and is then washed with altogether 50 ml of distilled water in two portions. 6.34 g (99%) of the title compound are obtained, melting at 144° C. with decomposition.

$[\alpha]_D^{20} = +52.4°$ (c=1, ethanol).

PREPARATION EXAMPLE 9

(−)-1α-(2′-carboxyethyl)-1α-ethyl-1,2,3,4,6,7,12,12bβ-octahydro-indolo(2,3-a)quinolizine.

Following the procedure described in Preparation Example 8, but starting from 6.8 g (0.02 moles) of (−)-1α-(methoxycarbonylethyl)-1β-ethyl-1,2,3,4,6,7,12,12bα-octahydro-indolo(2,3-a)quinolizine, 6.3 g (98.5%) of the title compound are obtained, melting at 144° C. with decomposition.

$[α]_D^{20} = -48.6°$ (c=1, ethanol).

PREPARATION EXAMPLE 10

(−)-1β-[(2′methoxycarbonyl-2′-hydroxyimino)-ethyl]-1α-ethyl-1,2,3,4,6,7,12,12bα-octahydro-indolo(2,3-a)quinolizine and its hydrochloride.

To 34 g (0.1 mole) of (−)-1β-(methoxycarbonylethyl)-1α-ethyl-1,2,3,4,6,7,12,12bα-octahydro-indolo(2,3-a)quinolizine, 20 ml of absolute toluene, a 55 to 60% toluene solution of 30 ml of tert.-butyl nitrite and then 17 g (0.15 moles) of potassium tert.-butylate are added. the mixture is stirred at 25° to 30° C. for 20 minutes, 150 ml of absolute methanol are slowly added and the mixture is then cooled to 20° C., is acidified up to pH=1 with concentrated hydrochloric acid, 50 ml of water are added and the mixture is stirred at +5° C. for 2 hours. The precipitate is filtered off, the KCl is washed out with water and the precipitate is dried. 32.5 g (80%) of the title compound are obtained, melting at 265° to 272° C. with decomposition.

$[α]_D^{20} = -57°$ (c=1, DMF).

From the hydrochloride obtained the free base is prepared by suspending the salt in 80 mo of methanol and adding a mixture of 25 ml of 25% aqueous ammonium hydroxide solution and 40 ml of water dropwise, under stirring. After one hour stirring it is cooled to 10° C., filtered, washed with water and dried. 24 to 25 g of the title compound are obtained, melting at 208° to 210° C. $[α]_D^{20} = -62°$ (c=1, DMF).

PREPARATION EXAMPLE 11

(−)-1β[(2′methoxycarbonyl-2′-hydroxyimino)-ethyl]-1α-octahydro-indolo(2,3-a)quinolizine.

(a) Following the procedure described in Preparation Example 10, but replacing K-tert.-butylate by 15 g of Na-tert.-butylate 24 g (60%) of the title compound are obtained.

(b) Following the procedure under point (a) but adding also 7 ml of absolute dimethyl formamide to the reacton mixture, 32.5 g (80%) of the title compound are obtained.

PREPARATION EXAMPLE 12

(−)-1β[(2′-ethoxycarbonyl-2′-hydroxyimino)-ethyl]-1α-ethyl-1,2,3,4,6,7,12,12bα-octahydro-indolo(2,3-a)quinolizine.

Following the procedure described in Preparation Example 10 but replacing methanol by 150 ml of absolute ethanol, 25 g of the HCl salt of the title compound (60%) are obtained, melting 257° to 260° C.

$[α]_D^{20} = -55°$ (c=1, DMF).

The corresponding base is set free in aqueous ethanol with a 25% amminium hydroxide solution, according to Preparation Example 10. 21 g of the title compound are obtained, melting at 172° to 173° C.

$[α]_D^{20} = -118°$ (c=1, CHCl₃).

PREPARATION EXAMPLE 13

(+)-1α[(2′-ethoxycarbonyl-2′-hydroxyimino)-ethyl]-1β-ethyl-1,2,3,4,6,7,12,12bβ-octahydro-indolo(2,3-a)quinolizine Following the procedure described in Comparative Example 10 but starting from 34 g of (+)-1α-(2′-methoxycarbonylethyl)-1β-ethyl-1,2,3,4,6,7,12,12bβ-octahydro-indolo(2,3-a)quinolizine and using 150 ml of absolute ethanol as an alcohol, 25.2 g (60%) of the hydrochloride of the title compound are obtained, melting at 258° to 260° C.

$[α]_D^{20} = +55°$ (c=1, DMF).

The corresponding base is set free in aqueous ethanol with a 25% ammonium hydroxide solution, according to Preparation Example 10. 21.3 g of the title compound are obtained, melting at 171° to 172° C.

$[α]_D^{20} = +118°$ (c=1, CHCl₃).

PREPARATION EXAMPLE 14

(−)-1α-[(2′-methoxycarbonyl-2′-hydroxyimino)-ethyl]-1β-ethyl-1,2,3,4,6,7,12,12bα-octahydro-indolo(2,3-a)quinolizine.

Following the procedure described in Preparation Example 10, but starting from 34 g (0.1 mole) of 1α-(2′-methoxycarbonylethyl)-1β-ethyl-1,2,3,4,6,7,12,12bα-octahydro-indolo(2,3-a)quinolizine, 24.3 g (60%) of the hydrochloride of the title compound are obtained, melting at 214° to 215° C.

$[α]_D^{20} = -46°$ (c=1, DMF).

The hydrochloride obtained is suspended in 50 ml of water, 100 ml of chloroform are added, whereupon the pH is adjusted to 9 with a 25% aqueous ammonium hydroxide solution. The chloroform phase is separated, the aqueous phase is extracted with 20 ml of chloroform. The combined organic phase is dried over sodium sulfate, evaporated in vacuo and the residue is recrystallized from 30 ml of dichloroethane. 19 g of the title compound are obtained, melting at 166° to 168° C.

$[α]_D^{20} = -54°$ (c−1, DMF)

PREPARATION EXAMPLE 15

(+)-1β-[(2′-methoxycarbonyl-2′-hydroxyimino)-ethyl]-1α-ethyl-1,2,3,4,6,7,12,12bβ-octahydro-indolo(2,3-a)quinolizine.

Following the procedure described in Preparation Example 10 but starting from 34 g (0.1 mole) of (+)-1β-(methoxycarbonylethyl)-1α-ethyl-1,2,3,4,6,7,12,12bβ-octahydro-indolo(2,3-a)quinolizine, 25 g (61.5%) of the hydrochloride of the title compound are obtained, melting at 214° to 215° C.

$[α]_D^{20} = +46°$ (c=1, DMF).

From the hydrochloride the corresponding free base is obtained, as described in Preparation Example 11. 19.2 g of the title compound are obtained, melting at 166° to 168° C.

$[α]_D^{20} = +53.2°$ (c=1, DMF).

PREPARATION EXAMPLE 16

(−)-1α[(ethoxycarbonyl-2′-hydroxyimino)-ethyl]-1β-ethyl-1,2,3,4,6,7,12,12bα-octahydro-indolo(2,3-a)quinolizine hydrochloride.

Following the procedure described in Preparation Example 10 but starting from 35.4 g (0.1 mole) of (−)-1α-(ethoxycarbonylethyl)-1β-ethyl-1,2,3,4,6,7,12,12bα-octahydro-indolo(2,3-a)quinolizine and using 150 ml of absolute ethanol as an alcohol, 23 g (55%) of the title compound are obtained, melting at 247° to 249° C.

$[α]_D^{20} = -44°$ (c=1, DMF).

PREPARATION EXAMPLE 17

(+)-1β-[(2'-ethoxycarbonyl-2'-hydroxyimino)-ethyl]-1α-ethyl-1,2,3,4,6,7,12,12bβ-octahydro-indolo(2,3-a)quinolizine hydrochloride.

Following the procedure described in Preparation Example 10 but starting from 35.4 g (0.1 mole) of (+)-1β-(2'-ethoxycarbonylethyl)-1α-ethyl-1,2,3,4,6,7,12,12bβ-octahydro-indolo(2,3-a)quinolizine and using 150 ml of absolute ethanol as an alcohol, 23.2 g of the title compound are obtained, melting at 248° to 249° C.

$[\alpha]_D^{20} = +45°$ (c=1, DMF).

PREPARATION EXAMPLE 18

Racemic trans 1-[(2'-ethoxycarbonyl-2'-hydroxyimino)ethyl]-1-ethyl-1,2,3,4,6,7,12,12b octahydro-indolo(2,3-a)quinolizine hydrochloride.

Following the procedure described in Preparation Example 10 but starting from 35.4 g (0.1 mole) of racemic trans 1-(ethoxycarbonylethyl)-1-ethyl-1,2,3,4,6,7,12,12b-octahydro-indolo(2,3-a)quinolizine and using 150 ml of absolute ethanol as an alcohol, 25.1 g (60%) of the title compound are obtained, melting at 226° to 228° C. (decomp.).

$[\alpha]_D^{20} = \pm \theta$ (c=1, DMF).

We claim:

1. A process for the preparation of a compound of the Formula I

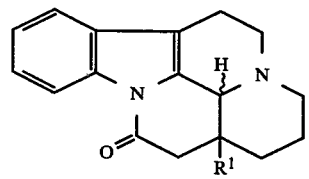

wherein $R^1$ is $C_1$ to $C_6$ alkyl, or an optical or geometric isomer thereof, which comprises the step of cyclizing a compound of the Formula II

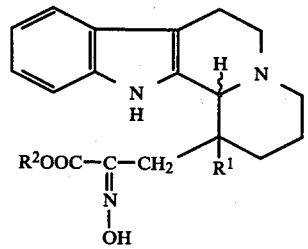

wherein $R^2$ is $C_1$ to $C_6$ alkyl, identical with or different from $R^1$ or a hydrogen atom, or an acid addition salt thereof, in a mono- or polyhydric alcohol solvent having a high boiling point, an ether thereof, or a mixture of said alcohol and said ether, in an inorganic base, at a temperature between 60° C. and 200° C.

2. The process defined in claim 1 wherein the compounds of the Formula II or an acid addition salt thereof, wherein $R^2$ is $C_1$ to $C_6$ alkyl, is subjected to basic hydrolysis at a temprature between 0° and 40° to yield a compound of the Formula II wherein $R^2$ is hydrogen, prior to undergoing the cyclization.

3. The process defined in claim 1, wherein an alkali metal hydroxide is used as the inorganic base.

4. A compound of the Formula II

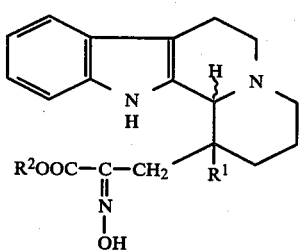

wherein $R^1$ is an alkyl group having 1-6 carbon atoms and $R^2$ is hydrogen or a salt, stereoisomer or geometrical isomer thereof.

* * * * *